US005646328A

United States Patent [19]

Deibele et al.

[11] Patent Number: 5,646,328
[45] Date of Patent: Jul. 8, 1997

[54] PROCESS FOR REMOVING BY-PRODUCTS FROM DIURETHANES

[75] Inventors: Ludwig Deibele; Oswald Wilmes; Jürgen Dahmer, all of Köln, Germany

[73] Assignee: Bayer Aktiengesellschaft, Leverkusen, Germany

[21] Appl. No.: 667,893

[22] Filed: Jun. 20, 1996

[30] Foreign Application Priority Data

Jun. 23, 1995 [DE] Germany ............... 195 23 386.7

[51] Int. Cl.⁶ .................................................. C07C 263/00
[52] U.S. Cl. ........................... 560/25; 560/115; 560/158; 560/345
[58] Field of Search ........................ 560/25, 115, 158, 560/345

[56] References Cited

U.S. PATENT DOCUMENTS

| 4,388,238 | 6/1983 | Heitkämper et al. | 260/239 E |
|---|---|---|---|
| 4,430,505 | 2/1984 | Heitkämper et al. | 560/24 |
| 4,497,963 | 2/1985 | Merger et al. | 560/115 |
| 4,596,678 | 6/1986 | Merger et al. | 560/344 CM |
| 4,596,679 | 6/1986 | Hellbach et al. | 560/344 |
| 4,713,476 | 12/1987 | Merger et al. | 560/115 |
| 4,851,565 | 7/1989 | Merger et al. | 560/115 |
| 5,087,739 | 2/1992 | Bohmholdt et al. | 560/345 |
| 5,360,931 | 11/1994 | Bohmholdt et al. | 560/344 |
| 5,386,053 | 1/1995 | Otterbach et al. | 560/344 |

FOREIGN PATENT DOCUMENTS

| 1144562 | 4/1983 | Canada . |
| 323514 | 7/1989 | European Pat. Off. . |

*Primary Examiner*—Samuel Barts
*Attorney, Agent, or Firm*—Joseph C. Gil; Lyndanne M. Whalen

[57] ABSTRACT

Low-boiling by-products are removed from diurethanes prepared by a phosgene-free process by carrier vapor distillation using alcohol vapor, preferably the vapor of the basic alcohol found in the diurethane, as the carrier vapor. The diurethanes freed of low-boiling by-products in this manner may be thermally decomposed to produce diisocyanates.

13 Claims, No Drawings

PROCESS FOR REMOVING BY-PRODUCTS FROM DIURETHANES

BACKGROUND OF THE INVENTION

The present invention relates to a new process for removing low-boiling by-products from a diurethane prepared by a phosgene-free process.

Diurethanes based on simple diisocyanates and low-boiling alcohols or phenols can be thermally decomposed to produce basic diisocyanates. One of the known methods for producing diisocyanates is preparation of a diurethane without the use of phosgene followed by thermal decomposition of that diurethane. Known methods for the phosgene-free preparation of diurethane include the reaction of a diamine with urea and alcohol (See, e.g., EP 18,586; EP 27,940; EP 27,953; EP 126,299; EP 126,300; EP 355,443; EP 568,782; and EP 566,925), reaction of a diamine with a carbamate and optionally an alcohol (EP 18,88; EP 27,952) and a reaction of a diamine with a carbonate (EP 323,514). The diurethanes prepared by any of these known methods contain a high-boiling fraction (e.g. oligoureas or polyureas) and impurities (derivatives of carbonic acid) which boil at a lower temperature than the diurethanes. To isolate the diurethanes, common separating techniques are generally applied.

EP 18,586 teaches that purification of the diurethane takes place after filtering off solids, e.g. by distilling off the excess alcohol and/or solvent and also the carbamate either formed as a by-product or used in excess. No data is given on the purity of the products obtained. The disadvantage of this disclosed process is that high-boiling impurities remain in the product. For complete separation of by-products which boil at a lower temperature than the diurethane by means of distillation, the reaction mixture must be exposed to heat for a certain length of time. This heating may cause the formation of additional decomposition products.

Crystallization or precipitation processes are also suggested as other purification possibilities. However, these purification processes are less economically viable for an industrial process due to the more complicated process engineering required.

EP 323,514; EP 27,940; EP 27,952; and EP 27,953 each teach that the product diurethane is worked-up by distillation. After distilling off the lower boiling solvents, auxiliary agents, reactants or intermediates, the urethanes are generally obtained as the last fraction or as the distillation residue. Before working up the product by means of distillation, insoluble components (e.g. insoluble catalysts) may be filtered off, if necessary. The disadvantage of these processes is that decomposition phenomena may be triggered in the products due to exposure to heat. This takes place in particular in the case of high-boiling diurethanes. Furthermore, the desired products may be contaminated by partial decomposition of the by-products during distillation.

EP 355,443 and EP 568,782 teach working-up of the diurethane containing mixture to remove unreacted alcohol by distillation. Then, N-unsubstituted carbamate and dialkyl carbonate are separated in a thin-film evaporator. The diurethane is obtained as the last distillation fraction.

In the process described in each of EP 126,299 and EP 126,300, a solvent (alcohol) is distilled out of the reaction mixture. In a second stage, the remainder of the solvent and derivatives of carbonic acid, dialkyl carbonates and/or alkyl carbamates originating from the preparation procedure are removed in a stripping column using an inert gas. Temperatures of up to 200° C. are used, so decomposition reactions may occur. In an industrial process, additional expense is incurred due to the need to purify the inert gas before discharging that inert gas to the environment. The produced purified in this manner may still contain oligo-urea/polyurethanes which are removed as the distillation residue in a further distillation step, e.g. in a thin-layer evaporator. Temperatures of up to 300° C. may be used.

EP 566,925 teaches separation of the alcohol, dialkyl carbonate and alkyl carbamate by reducing the pressure from the level using during the preparation stage (12 bar) to a pressure of 50 mbar. This process is very complicated from an engineering perspective. Further, complete elimination of the dialkyl carbonate or alkyl carbamate is not achieved. We have found that the product treated in accordance with this known procedure still contains up to 5% of these by-products which are subsequently found in the isocyanate produced by thermal decomposition of the urethane.

SUMMARY OF THE INVENTION

It is an object of the present invention to provide a process for effectively removing low-boiling by-products from a diurethane produced by a phosgene-free process.

It is also an object of the present invention to provide a process for the production of diurethanes which are substantially free from low-boiling by-products which process is carried out under relatively mild processing conditions.

It is another object of the present invention to provide a process for producing diurethanes which are substantially free of low boiling by-products without the risk of premature thermal decomposition of the diurethane.

These and other objects which will be apparent to those skilled in the art are accomplished by removing the low-boiling by-products from the diurethane by a carrier vapor distillation using alcohol as the vapor carrier. This process is carried out at temperatures which are well below conventional decomposition temperatures. The use of alcohol as the carrier vapor counteracts unwanted decomposition of the diurethane in the sense of the law of mass action.

DETAILED DESCRIPTION OF THE INVENTION

The present invention relates to a process for removing low-boiling by-products from diurethanes which have been prepared by a phosgene-free method. The diurethanes which may be treated in accordance with the process of the present invention are represented by the general formula (I)

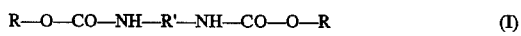

$$R-O-CO-NH-R'-NH-CO-O-R \quad (I)$$

in which

R represents an alkyl group having from 1 to 6 carbon atoms, a cycloalkyl group having from 5 to 6 carbon atoms or a phenyl group and R' represents a group which may be produced by removing the isocyanate groups from an organic diisocyanate having a molecular weight in the range from 140 to 300.

These diurethanes are subjected to carrier vapor distillation using an alcohol vapor as the vapor carrier. The low-boiling by-products are removed as carrier vapor distillate. The diurethanes freed of by-products are recovered as the carrier vapor distillation residue.

The present invention also relates to the use of the diurethanes represented by formula (I), from which the low-boiling by-products have been removed, for preparing diisocyanates by thermal decomposition. In a preferred embodiment of this invention, by-products having boiling points higher than that of the diurethane are removed from the diurethane by distillation before that diurethane is thermally decomposed.

The starting materials for the process of the present invention are industrial mixtures such as those produced by any of the known methods for phosgene-free preparation of diurethanes represented by formula (I). The main products in this industrial mixture correspond to formula (I). The preferred diurethanes are those in which R represents an alkyl group having from 1 to 4 carbon atoms and R' represents an aliphatic or cycloaliphatic hydrocarbon group having from 6 to 15 carbon atoms, most preferably those hydrocarbon groups linking the isocyanate groups in 1,6-diisocyanatohexane, bis-(4-isocyanatocyclohexyl)-methane, 1-isocyanato-3,3,5-trimethyl-5-isocanatomethyl-cyclohexane or 2-methyl- and/or 4-methyl-1,3-diisocyanatocyclohexane (hydrogenated toluylene diisocyanate).

Specific examples of suitable starting materials for the process of the present invention include those whose main component corresponding to formula (I) is butanediurethane-1,4; 1 -methylpentanediurethane-1,5; hexanediurethane-1,6,2,2,4- or 2,4,4-trimethylhexanediurethane-1,6; cyclohexanediurethane-1,3; cyclohexanediurethane-1,4; 2-methyl- and/or 4-methyl-cyclohexanediurethane-1,3 (hydrogenated toluylenediurethane); 1,3- and 1,4-bisalkoxycarbonylaminocyclohexane; bis-(4-alkoxycarbonyl-aminocyclohexyl)-methane; bis-(4-alkoxycarbonylaminocyclohexyl)-methane; bis-(4-alkoxy-carbonylamino-3-methylcyclo-hexyl)-methane; 3-alkoxy-carbonyl-aminomethyl-3,5,5-trimethylcyclohexyl-urethane (isophoronediurethane); and 3- and/or 4-alkoxycarbonylamino-methyl-1-methylcyclohexylurethane. The basic alcohol component of these diurethanes is preferably methanol, ethanol or n-butanol.

Particularly preferred industrial mixtures for use in the process of the present invention are those whose main component represented by formula (I) is 1,6-bis-($C_1$–$C_4$-alkoxycarbonylamino)-hexane (HDU); 1-($C_1$–$C_4$-alkoxycarbonylamino)-3,3,5-trimethyl-5-($C_1$–$C_4$-alkoxycarbonylamino)-cyclohexane (IPDU); or bis-[4-($C_1$–$C_4$-alkoxycarbonylamino)-cyclohexyl]-methane. The industrial mixtures produced during the various phosgene-free processes for producing the diurethanes of formula (I) generally contain, each being with respect to the weight of diurethanes of the formula (I), up to 25% by weight, preferably up to 15% by weight (based on weight of diurethane corresponding to formula (I)), of by-products having boiling points below the boiling point of the diurethane. Examples of such low-boiling by-products are alkyl carbamates and dialkyl carbonates. These industrial mixtures also generally contain up to 25% by weight, preferably up to 15% by weight (based on weight of diurethane corresponding to formula (I)) of by-products which have boiling points higher than that of the diurethane. Examples of such high boiling by-products include those represented by the formula

ROCONH—R'—[NHCONH—R']$_n$—NHCOOR($n \geq 1$)

In general, excess alcohol present in the crude mixture is removed by distillation, after its production, down to a residual amount of at most 5% by weight (based on the weight of diurethane represented by formula (I)).

The starting mixtures used in the process of the present invention may be crude mixtures from which most of the excess alcohol has been removed. It is also possible, however, to use starting mixtures from which the high-boiling by-products have previously been removed. This type of mixture may be obtained by removing excess alcohol from the mixture produced during the production process and then subjecting the mixture to a thin-layer distillation in which all products that boil at a temperature lower than the high-boiling products mentioned, are obtained as the thin-layer distillate. In addition to diurethanes represented by formula (I), the thin layer distillate will contain the by-products which boil at a lower temperature than the diurethanes. The thin layer distillate is therefore useful as a starting material for the process of the present invention.

To perform the alcohol vapor distillation in accordance with the present invention, vapors of alcohols represented by formula (II)

R"—OH    (II)

in which

R" represents an alkyl group having from 1 to 6 carbon atoms or a cycloalkyl group are used.

It is preferred that R" represent the same group as is represented by R in formula (I) for the diurethane being treated in accordance with the process of the present invention.

The process of the present invention is preferably carried out in distillation columns which are filled with plates and/or packing. The starting material from which low-boiling by-products is to be removed is fed to the column from above as a liquid while the alcohol vapor is introduced to the column from below. The vapor flows through the column as a countercurrent to the liquid and thus picks up the by-products which boil at a lower temperature than the diurethane. The alcohol vapor containing low-boiling by-products leaves the column at the head and is then condensed. The diurethane, containing substantially no low-boiling components, is collected as a liquid at the base of the column.

The operating pressure for the column is selected so that the boiling point of the alcohol represented by formula (II) at this pressure is above the solidification point of the diurethane. In general, the pressure is below standard atmospheric pressure (1013 mbar). The temperature at the head of the column is generally from 100° to 200° C. The temperature of the alcohol vapor is generally from 10° to 50° C. above the boiling point of the alcohol at the corresponding pressure. The amount of alcohol used to produce the carrier vapor is generally such that the ratio by volume, each with respect to liquid, of carrier-vapor alcohol to starting material (diurethanes of the formula (I) containing low-boiling and optionally high-boiling components) is from 0.3:1 to 5:1, preferably from 0.5:1 to 2:1.

The concentration of alcohol in the purified diurethane can be varied by the degree of superheating of the alcohol vapor. The alcohol concentration is preferably between 0 and 10%. To achieve 0%, the degree of superheating of the alcohol vapor must be great enough to evaporate the low-boiling components.

If the starting material used for carrier vapor distillation still contains by-products whose boiling point is above that of the diurethane being purified, any of the known high-boiling component isolation procedures may be performed after the vapor carrier distillation. Such known isolation procedures include distillation, preferably thin-layer distillation, with isolation of the high-boiling components as the distillation residue.

Having thus described our invention, the following Example is given as being illustrative thereof. All percentage data given in the Example are percentages by weight.

EXAMPLE

The carrier vapor distillation (packed column with a diameter of 50 mm and a depth of packing of 2 m) procedure was performed at 150 mbar. 500 ml/h of starting material comprising 1,6-bis-(n-butoxycarbonyl-amino)-hexane with a concentration (based on the weight of this diurethane) of lower-boiling components of 3.5 wt. % (2.2% by weight n-butyl carbamate and 1.3% by weight di-n-butyl carbonate) were supplied to the head of the column. 500 ml/h (with respect to liquid) of n-butanol superheated to 150° C. were used as the carrier vapor and fed to the base of the column. This corresponded to a ratio by volume of feedstock to carrier vapor of 1:1. At the upper end of the carrier vapor distillation, the n-butanol vapor contained 3.5% of low-boiling components (2.2% by weight butyl carbamate, 1.3% by weight dibutyl carbonate). The purified hexanediurethane-1,6 flowed from the base of the column in a pure form. The lower-boiling by-products were no longer detectable (limit of detection of each =0.1%).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for removing low-boiling by-products from a diurethane prepared by a phosgene-free process which diurethane is represented by the general formula (I)

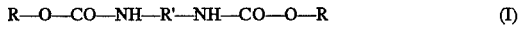

R—O—CO—NH—R'—NH—CO—O—R  (I)

in which

R represents an alkyl group having from 1 to 6 carbon atoms, a cyclo-alkyl group having from 5 to 6 carbon atoms or a phenyl group and R' represents a group obtainable by removing isocyanate groups from an organic diisocyanate which group has a molecular weight in the range from 140 to 300, comprising a) subjecting the diurethane containing by-products to carrier vapor distillation using alcohol vapor as the carrier vapor, b) recovering the low-boiling by-products removed as carrier vapor distillate, and c) recovering the diurethane as the residue.

2. The process of claim 1 in which the alcohol used as the carrier vapor is represented by formula (II)

R"—OH  (II)

in which

R" represents the same group or groups as the R groups in the diurethane represented by formula (I) which is being subjected to vapor carrier distillation.

3. The process of claim 2 in which the diurethane is represented by formula (I) in which R represents a $C_1$–$C_4$-alkyl group and R" represents the hydrocarbon group linking the isocyanate groups in 1,6-diisocyanatohexane, bis-(4-isocyanatocyclohexyl)-methane, 1-isocyanato-3,3,5-trimethyl-5-isocanatomethyl-cyclohexane or 2-methyl- and/or 4-methyl-1,3-diisocyanatocyclohexane.

4. The process of claim 3 in which the carrier vapor distillation is carried out by (1) feeding the diurethane containing by-products to a distillation column at its head, (2) removing the carrier vapor containing by-products from the head of the distillation column, (3) feeding the carrier vapor to the distillation column at its bottom, and (4) removing the diurethane product from the bottom of the column.

5. The process of claim 4 in which the diurethane containing by-products is the crude product from a phosgene-free production of a diurethane represented by formula (I) in which (i) up to 5 wt. % of alcohol represented by the formula ROH, (ii) up to 25 wt. % of by-products having a boiling point below that of the diurethane of formula (I) and (iii) up to 25 wt. % of by-products with a boiling point above that of the diurethane of formula (I) are present.

6. The process of claim 5 in which any by-products having a boiling point above that of the diurethane represented by formula (I) have been removed from the starting material by distillation prior to step a).

7. A process for the production of diisocyanates comprising thermally decomposing the diurethane recovered in step c) of claim 1.

8. The process of claim 1 in which the diurethane is represented by Formula (I) in which R represents a $C_1$–$C_4$-alkyl group and R' represents the hydrocarbon group linking the isocyanate groups in 1,6-diisocyanatohexane, bis-(4-isocyanatocyclohexyl)-methane, 1-isocyanato-3,3,5-trimethyl-5-isocyanatomethyl-cyclohexane, 2-methyl-1,3-diisocyanatocyclohexane and/or 4-methyl-1,3-diisocyanatocyclohexane.

9. The process of claim 1 in which the carrier vapor distillation is carried out by (1) feeding the diurethane containing by-products to a distillation column at its head, (2) removing the carrier vapor containing by-products from the head of the distillation column, (3) feeding the carrier vapor to the distillation column at its bottom, and (4) removing the diurethane product from the bottom of the column.

10. The process of claim 2 in which the carrier vapor distillation is carried out by (1) feeding the diurethane containing by-products to a distillation column at its head, (2) removing the carrier vapor containing by-products from the head of the distillation column, (3) feeding the carrier vapor to the distillation column at its bottom, and (4) removing the diurethane product from the bottom of the column.

11. The process of claim 1 in which the diurethane containing by-products is the crude product from a phosgene-free production of a diurethane represented by Formula (I) in which up to 5 wt. % of alcohol represented by the formula ROH, up to 25 wt. % of by-products having a boiling point below that of the diurethane of Formula (I), and (iii) up to 25 wt. % of by-products with a boiling point above that of the diurethane of Formula (I) are present.

12. The process of claim 2 in which the diurethane containing by-products is the crude product from a phosgene-free production of a diurethane represented by Formula (I) in which (i) up to 5 wt. % of alcohol represented by the formula ROH, (ii) up to 25 wt. % of by-products having a boiling point below that of the diurethane of Formula (I), and (iii) up to 25 wt. % of by-products having a boiling point above that of the diurethane of Formula (I) are present.

13. The process of claim 3 in which the diurethane containing by-products is the crude product from a phosgene-free production of a diurethane represented by Formula (I) in which (i) up to 5 wt. % of alcohol represented by the formula ROH, (ii) up to 25 wt. % of by-products having a boiling point below that of the diurethane of Formula (I), and (iii) up to 25 wt. % of by-products having a boiling point below that of the diurethane of Formula (I) are present.

* * * * *